(12) United States Patent
Schneider

(10) Patent No.: US 8,318,073 B2
(45) Date of Patent: Nov. 27, 2012

(54) NON-SLIP ACTIVATION MEMBERS

(75) Inventor: Uwe Schneider, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/951,563

(22) Filed: Nov. 22, 2010

(65) Prior Publication Data

US 2011/0064837 A1   Mar. 17, 2011

Related U.S. Application Data

(62) Division of application No. 11/493,496, filed on Jul. 26, 2006, now Pat. No. 7,857,609.

(51) Int. Cl.
*B29C 55/00* (2006.01)
(52) U.S. Cl. .................. 264/288.4; 264/290.2; 264/291
(58) Field of Classification Search .................. 264/286, 264/287, 288.4
See application file for complete search history.

(56) References Cited

U.S. PATENT DOCUMENTS

| | | | |
|---|---|---|---|
| 4,087,226 A | 5/1978 | Mercer | |
| 4,517,714 A | 5/1985 | Sneed et al. | |
| 5,427,462 A * | 6/1995 | Jackson et al. | 400/579 |
| 6,500,377 B1 | 12/2002 | Schneider et al. | |
| 6,572,598 B1 | 6/2003 | Ashton et al. | |
| 2003/0207640 A1* | 11/2003 | Anderson et al. | 442/394 |
| 2008/0023879 A1 | 1/2008 | Schneider | |

FOREIGN PATENT DOCUMENTS

| | | |
|---|---|---|
| EP | 1 127 825 A2 | 8/2001 |
| WO | WO 2005/065919 A1 | 7/2005 |

OTHER PUBLICATIONS

PCT International Search Report, dated Apr. 12, 2007, 11 pages.

* cited by examiner

*Primary Examiner* — Yogendra Gupta
*Assistant Examiner* — Robert J Grun
(74) *Attorney, Agent, or Firm* — Amy M. Foust; Abbey A. Lopez

(57) ABSTRACT

A mechanical activation system has a first activation member, a second activation member, an activation zone, and a non-slip zone. The first activation member has a first plurality of teeth, and the second activation member has a second plurality of teeth. The first plurality of teeth is capable of intermeshing with the second plurality of teeth. The activation zone includes a first portion of the first plurality of teeth and a first portion of the second plurality of teeth. The first portion of the first plurality of teeth and the first portion of the second plurality of teeth include teeth having continuous tips. The first non-slip zone includes a second portion of the first plurality of teeth or a second portion of the second plurality of teeth. The second portion includes a tooth having a discontinuous tip.

14 Claims, 10 Drawing Sheets

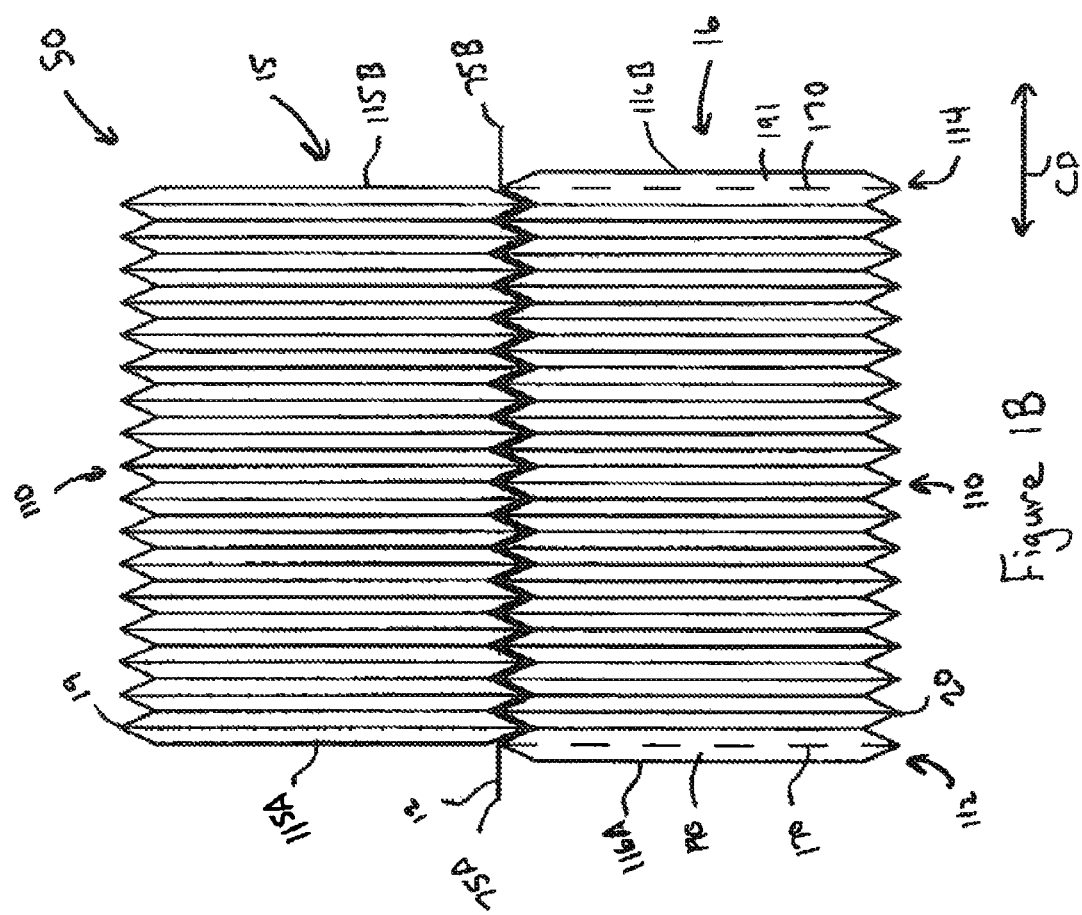

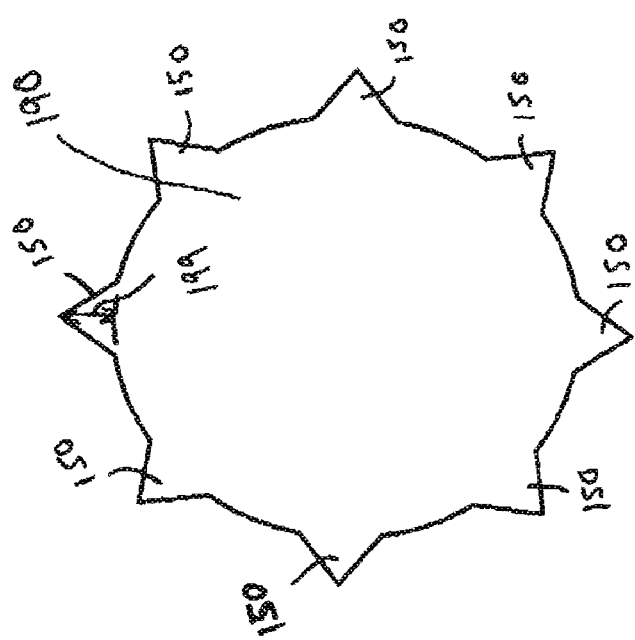

NON-SLIP ACTIVATION MEMBERS

CROSS-REFERENCE TO RELATED APPLICATIONS

This application is a divisional of U.S. patent application Ser. No. 11/493,496, filed on Jul. 26, 2006 now U.S. Pat. No. 7,857,609, which is hereby incorporated by reference in its entirety.

FIELD OF THE INVENTION

The present invention relates to a method and apparatus for activating a moving web such as a nonwoven web, an elastomeric web, laminate webs, and/or webs of disposable absorbent articles. More particularly, the present invention relates to a method and apparatus for activating a moving web while reducing the slippage of the moving web with regard to the activation members.

BACKGROUND OF THE INVENTION

In order to provide fit and comfort to a wearer, many commercially available disposable absorbent articles, e.g., diapers, include elastomeric elements. For example, a diaper may include elastomeric elements in leg regions and a waist region of the diaper, thereby allowing the diaper to extend and contract about the leg regions and waist region of a wearer. The capability to extend and contract about the leg regions and the waist region can allow the disposable absorbent diaper to fit a wide range of wearers.

In some instances, the elastomeric elements can be manufactured via a mechanical activation process. The mechanical activation process typically involves meshing a web of material, e.g., a laminate web comprising a nonwoven and elastic, between activation members. The activation members can have protruding engagement elements. Generally, the engagement elements of the activation members intermesh. As the web of material is intermeshed between the engagement elements, tensile forces are applied to the web of material such that the nonwoven is permanently elongated at least to a certain degree. The nonwoven is elongated so that upon release of the applied tensile forces, the web of material generally will not fully return to its original undistorted configuration.

However, the intermeshing engagement elements generally provide no safeguard against slippage of the web of material with respect to the activation members. For example, in some cases, the web of material can slip in a cross machine direction with respect to the activation members. In general, the slippage occurs at the outermost intermeshing engagement elements of the activation members.

This slippage can reduce the amount of strain applied to the web of materials proximate to the outermost intermeshing engagement elements. Unfortunately, the reduced strain can limit the amount of elasticity applied to the web of materials proximate to the outermost engagement elements.

Accordingly, there is a need for a method and apparatus which can reduce the amount of slipping by the web of materials on the outermost engagement elements of the activation members.

SUMMARY OF THE INVENTION

A mechanical activation system according to the present invention can reduce the slippage of a substrate which experiences the mechanical activation process. The mechanical activation system comprises a first member comprising a first plurality of teeth and a second activation member comprising second plurality of teeth. The first plurality of teeth and the second plurality of teeth are capable of intermeshing with one another.

The mechanical activation system further comprises an activation zone and a first non-slip zone. The activation zone comprises a first portion of the first plurality of teeth and a first portion of the second plurality of teeth. The first portion of the first plurality of teeth and the first portion of the second plurality of teeth include teeth having continuous tips. The first non-slip zone comprises a second portion of the first plurality of teeth or a second portion of the second plurality of teeth, wherein the second portion includes a tooth having discontinuous tip.

Additionally, a method performed in accordance with the present invention can reduce the slippage of a substrate experiencing the mechanical activation process. A method of mechanically activating a substrate comprises the steps of obtaining a substrate and providing the substrate to a mechanical activation system. The substrate is then intermeshed between a first plurality of teeth of a first activation member and a second plurality of teeth of a second activation member. The slippage of the substrate with respect to the first activation member and the second activation member is then reduced.

BRIEF DESCRIPTION OF THE DRAWINGS

FIG. 1B is an elevation view showing the mechanical activation system of FIG. 1A.

FIG. 1G is an elevation view showing a side of an exemplary tooth of a non-slip zone of the mechanical activation system of FIG. 1A.

DETAILED DESCRIPTION OF THE INVENTION

Definitions

Figure 1A:
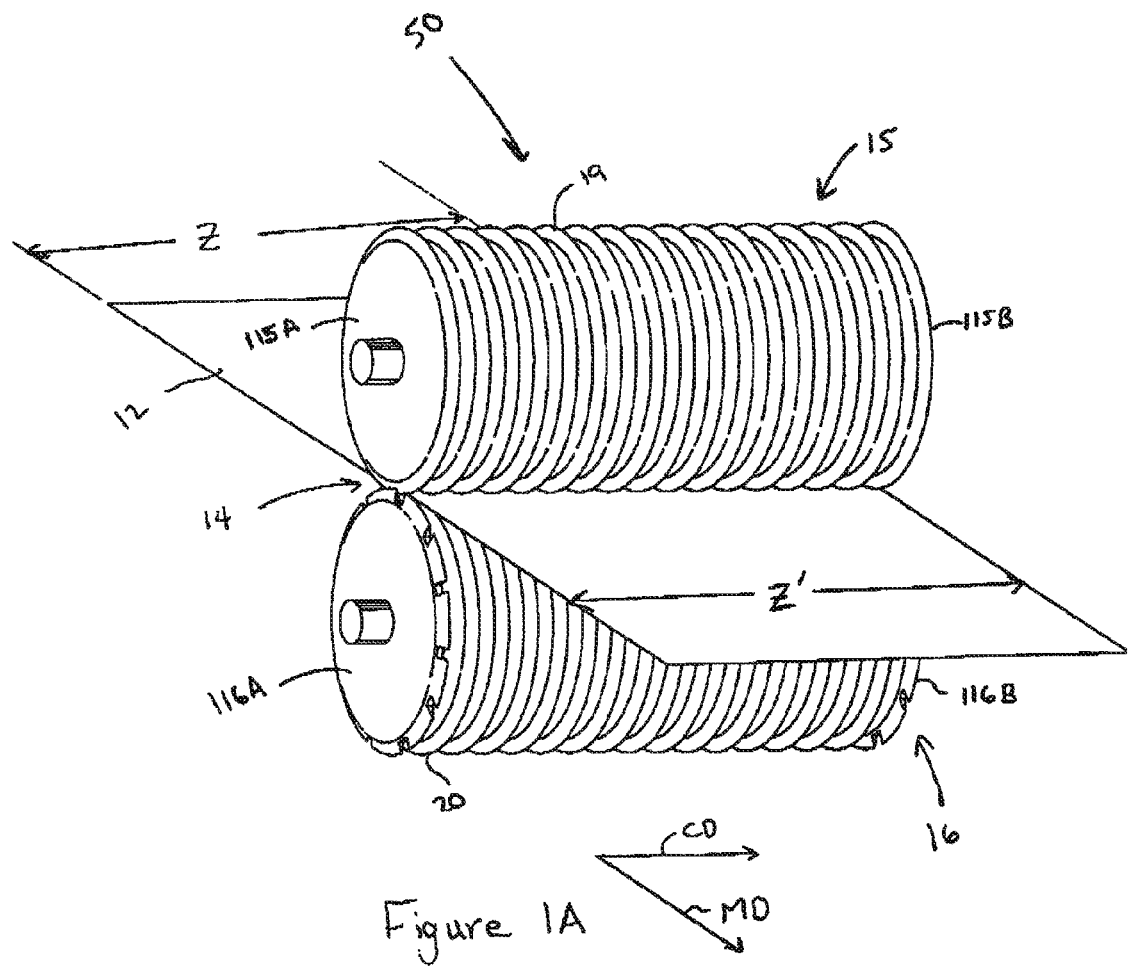
FIG. 1A is an isometric view showing an embodiment of a mechanical activation system constructed in accordance with the present invention.

The terms "activating", "activation", or "mechanical activation" refer to the process of making a substrate, or an elastomeric laminate more extensible than it was prior to the process.

The terms "corrugations" or "rugosities" are used to describe hills and valleys that occur in a substrate or in a laminate structure either via an activation process or a live stretch process. In an activation process, a laminated structure having an elastomeric material and an extensible material are secured together in a face to face relationship and subjected to incremental strain. The extensible material, upon stretching, can permanently elongate at least to a certain degree such that upon release of an applied tensile force to the laminated structure, the extensible material will not fully return to its original undistorted configuration. In contrast, the use of live stretch involves attaching a non-elastic substrate and an elastic element while the elastic is under tension. Once the elastic is bonded to the non-elastic substrate and at least a portion of the tension in the elastic element is removed, the non-elastic substrate gathers between the locations where it is bonded to the elastic thereby forming corrugations. Note that neither term, i.e. "corrugations" or "rugosities" mandates that either the hills or valleys created are uniform in nature.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The term "disposable" is used herein to describe products, which generally are not intended to be laundered or otherwise restored and reused for their original function. They are typically intended to be discarded after about 1 or 2 uses. It is preferred that such disposable articles be recycled, composted or otherwise disposed of in an environmentally compatible manner.

A "disposable absorbent article" refers to an article device that normally absorbs and/or retains fluids. In certain instances, the phrase refers to articles that are placed against or in proximity to the body of the wearer to absorb and contain the excreta and/or exudates discharged from the body, and includes such personal care articles as baby diapers, baby training pants, adult incontinence articles, feminine hygiene articles, baby swim diapers, wound dressings, and the like. A disposable absorbent article may be worn by infants and other incontinent persons about the lower torso.

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "machine direction" is used herein to refer to the direction of material flow through a process. The machine direction is also the primary direction of fiber orientation in the nonwoven. If fiber orientation is not clear by visual inspection of the nonwoven, then the machine direction corresponds to the direction having the highest peak tensile force.

The term "cross direction" is used herein to refer to a direction that is perpendicular to the machine direction.

Description

The apparatus of the present invention can reduce the slippage of a web of material during a mechanical activation process. The apparatus of the present invention can be utilized in the manufacture of a variety of consumer and commercial goods. For example, the elastically extensible side panels of a disposable diaper may be mechanically activated prior to being joined to the chassis of the diaper or post joining to the chassis of the diaper.

An example of a mechanical activation system 50 is shown in FIG. 1A. As shown, the mechanical activation system 50 may comprise a first activation member 15 and a second activation member 16. As shown, in some embodiments, the first activation member 15 and the second activation member 16 may comprise rolls which rotate about a first axis of rotation 133 and a second axis of rotation 134, respectively.

The first activation member 15 may comprise a plurality of engagement elements 19, and the second activation member 16 may comprise a plurality of engagement elements 20. Additionally, as shown, the first activation member 15 comprises a first end 115A and a second end 115B, and the second activation member 16 comprises a first end 116A and a second end 116B. As shown, in some embodiments, the each of the plurality of engagement elements 19 can be aligned such that each of the plurality of engagement elements rotates about the first axis of rotation 133. Additionally, as shown, in some embodiments, each of the plurality of engagement elements 20 can be aligned such that each of the plurality of engagement elements rotates about the second fixed axis of rotation 134.

As shown, a substrate 12 can pass through a nip 14 between the first activation member 15 and the second activation member 16 having an initial width Z. The initial width Z as shown is generally parallel to a CD direction. As the substrate 12 passes through the nip 14, the substrate 12 is elongated by the intermeshing of the substrate 12 between the engagement elements 19 and 20 of the first activation member 15 and the second activation member 16, respectively. Downstream of the nip 14, the substrate 12 generally comprises corrugations and a final width Z'. The final width Z' is greater than the initial distance Z.

As shown in FIG. 1B, the mechanical activation system 50 may comprise a plurality of zones. For example, as shown, the mechanical activation system 50 may comprise an activation zone 110, a first non-slip zone 112, and a second non-slip zone 114. As shown, in some embodiments, the activation zone 110 can be disposed between the first and second non-slip zones 112 and 114. Additionally, as shown, in some embodiments, the first non-slip zone 112 can be disposed proximate to the first end 116A of the second activation member 16. Also, in some embodiments, the second non-slip zone 114 can be disposed proximate to the second end 1163 of the second activation member 16. Embodiments are contemplated where the first non-slip zone 112 is disposed proximate to the first end 115A of the first activation member 15 and/or where the second non-slip zone 114 is disposed proximate to the second end 115B of the first activation member 15.

The activation zone 110 may include a portion of the plurality of the second engagement elements 20 and a portion of the plurality of first engagement elements 19. Embodiments are contemplated where the activation zone 110 comprises all of the plurality of first engagement elements 19 or all of the plurality of second engagement elements 20.

As shown, in some embodiments, the first non-slip zone 112 may comprise a portion of the second activation member 16. Similarly, the second non-slip zone 114 may comprise a portion of the second activation member 16. Embodiments are contemplated where the first non-slip zone 112 comprises a portion of the first activation member 15 and a portion of the second activation member 16. Similarly, embodiments are contemplated where the second non-slip zone 114 comprises a portion of the first activation member 15 and a portion of the second activation member 16. Also, embodiments are contemplated where the first non-slip zone 112 comprises a portion of the second activation member 16 only and the second non-slip zone 114 comprises a portion of the first activation member 15 only and vice versa.

As shown, in some embodiments, the first non-slip zone 112 may include an engagement element 190 of the plurality of the second engagement elements 20. Similarly, the second non-slip zone 114 may include an engagement element 191 of the plurality of the second engagement elements 20. Embodiments are contemplated where the first non-slip zone 112 and/or the second non-slip zone 114 comprise a tooth from the plurality of first teeth 19.

Additionally, embodiments are contemplated where the first non-slip zone 112 comprises more than one engagement element which is configured similarly to the tooth 190. Embodiments are contemplated where the second non-slip zone 114 comprises more than one engagement element configured similarly to the tooth 191. For example, in some embodiments, the first non-slip zone 112 may comprise the two outermost engagement elements proximate to the first end 116A of the second activation member 16. Similarly, embodiments are contemplated where the activation zone 110 comprises at least one tooth which is configured similar to a tooth 180 (shown in FIGS. 1C and 1D).

Figure 1D:
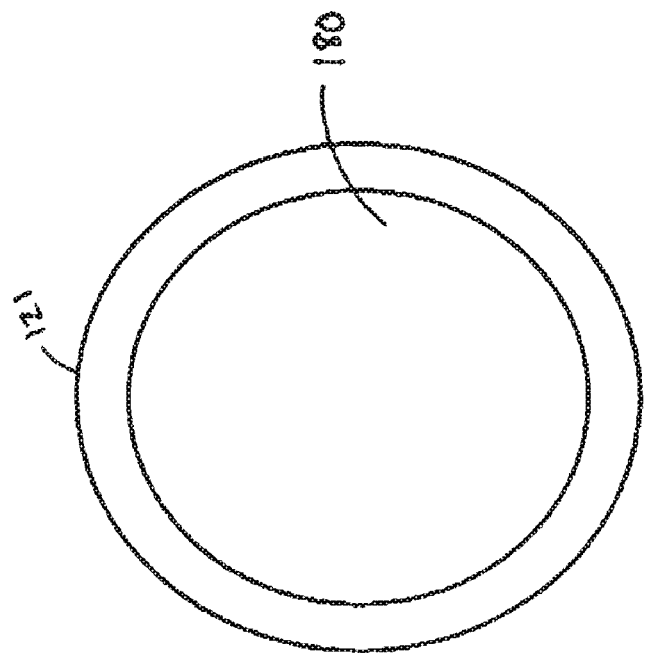
FIGS. 1C and 1D are elevation views showing a side of an exemplary tooth of an activation zone of the mechanical activation system of FIG. 1A.
Figure 1C:

An example of the engagement element 180 disposed within the activation zone 110 is provided with regard to FIGS. 1C and 1D. In some embodiments, the engagement element 180 of the activation zone 110 (shown in FIG. 1B) may comprise a tip 121. As shown, in some embodiments, the tip 121 may extend continuously about the circumference of the engagement element 180.

Figure 1F:
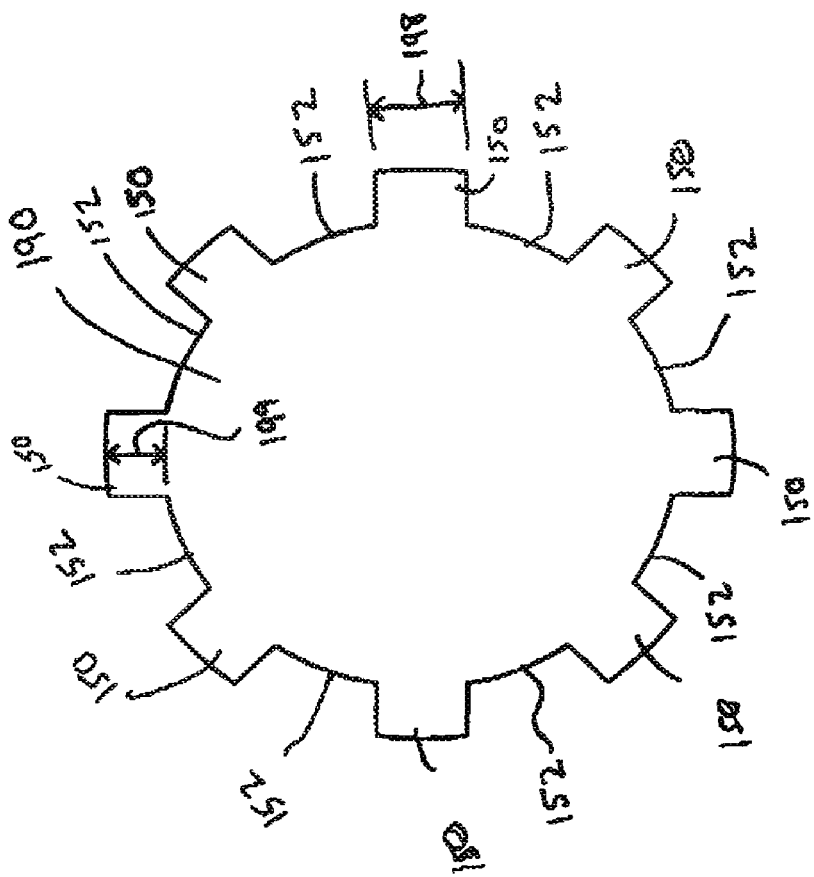
FIGS. 1E and 1F are elevation views showing a side of an exemplary tooth of a non-slip zone of the mechanical activation system of FIG. 1A.
Figure 1E:
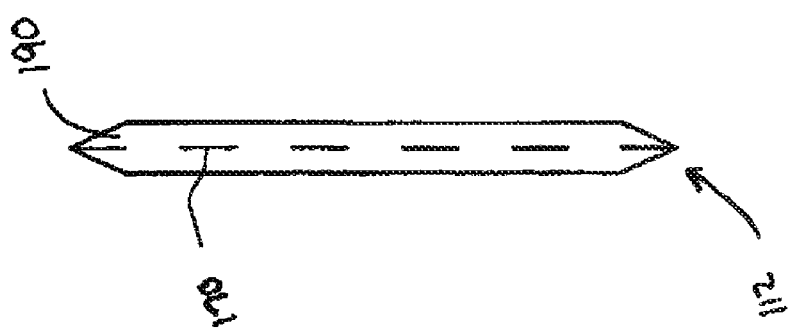

As shown in FIGS. 1E and 1F, in some embodiments, the first non-slip zone 112 may comprise the engagement element 190. As shown, in contrast to the engagement element 180 (shown in FIGS. 1C and 1D), the engagement element 190 may comprise a tip 170 which does not extend continuously about the circumference of the engagement element 190. The engagement element 191 can be configured in a similar manner to engagement element 190 and may be comprised by the second non-slip zone 114.

As shown in FIG. 1F, the addition of the discontinuous tip 170 can produce a plurality of non-slip elements 150 and a plurality of recesses 152. The non-slip elements 150, as shown, in some embodiments, may comprise a square shape. However, any suitable shape known in the art can be utilized. For example, the non-slip elements 150 may comprise a triangular shape, a circular shape, an arcuate shape, a rectangular shape, rhomboidal shape, trapezoidal shape, polygonal shape, or any combination thereof.

It has been discovered that a larger number of non-slip elements 150 can have a greater impact on reducing slippage than does a smaller number of non-slip elements 150. Additionally, it has been discovered that non-slip elements 150 comprising a smaller length 198 can be more effective at reducing slippage than non-slip elements 150 comprising a larger length 198. For example, an engagement element having a plurality of non-slip elements 150 having a length 198 of less than about 1 mm can be more effective at reducing slippage than an engagement element having a plurality of non-slip elements 150 having a length 198 of about 5 mm. As another example, it has been discovered that non-slip elements 150 having a sharp angled tip, as shown in FIG. 1G, can provide reduced slippage of the nonwoven relative to the activation members.

Additionally, while the embodiment shown in FIG. 1F shows a plurality of non-slip elements 150, any suitable number of non-slip elements 150 may be utilized. Depending on the specific application, a single non-slip element 150 may provide some reduction in the amount of slippage of the substrate 12 (shown in FIGS. 1A and 1B) from slipping. In other examples, a plurality of non-slip elements 150 may be required.

For the purposes of the present invention, a tip 170 which does not extend continuously about the circumference of engagement element shall be termed discontinuous. Within the context of discontinuous, minor asperities in the tip 170 will not constitute a discontinuous tip. A discontinuous tip comprises purposefully placed interruption(s) in the tip 170 which produces a non-slip element. Any discontinuities of the present invention should cause recesses which have a depth 199 of at least about 0.2 mm to about 5 mm, or any individual number within the range. In some embodiments, the depth 199 can be between about 1 mm to about 3 mm.

The depth 199, for the rotational activation systems shown with regard to FIGS. 1A-1F and 2A-2B, is the maximum linear distance from a point at the smallest radial distance to a point at the largest adjacent radial distance. The depth 199 is generally co-linear with the radius of an activation member.

Alternatively or in conjunction with the non-slip elements, the first non-slip zone 112 and/or the second non-slip zone 114 may comprise engagement elements having an increased coefficient of friction near the engagement element tip. For example, the tip of one or more engagement elements may comprise a surface finish which is sufficiently rough to cause interlocking between the engagement element tip and the fibers of the substrate 12 (shown in FIGS. 1A and 1B). As another example, the tip of one or more engagement elements may comprise a high friction coating which can reduce the slippage of the substrate 12 (shown in FIGS. 1A and 113) with respect to the activation members 15 (shown in FIGS. 1A and 1B) and 16 (shown in FIGS. 1A and 1B). Suitable examples of high friction coatings are Plasma Coat™ 402, Plasma Coat™ 12036 available from Plasma Coating Inc. of Arlington, Tenn.

The coefficient of friction of such coatings is typically measured against nonwoven materials. In some embodiments, the coefficient of friction is in the range of about 0.8 to about 1.0, or any individual number within the range. By way of contrast, conventional activation members having a smooth polished surface (stainless steel or anodized aluminum) typically exhibit coefficients of friction in the range from about 0.25 to about 0.3 against nonwoven materials.

An added benefit to the treatments mentioned above which increase the coefficient of friction of the engagement elements is that all of the engagement elements of the activation members can be treated without impacting the activation process, i.e. creating discontinuous activation. In contrast, embodiments utilizing the non-slip elements described above are preferably limited to a portion of the engagement elements and not all. Where the non-slip elements are utilized across all engagement elements, the resulting substrate can have discontinuous activation which may not be desirable.

Referring again to FIG. 1B, the first end 115A of the first activation member 15 and the first end 116A of the second activation member 16 are generally disposed inboard from a first longitudinal end 75A of the substrate 12 during processing. Similarly, the second end 115B of the first activation member 15 and the second end 116B of the second activation member 16 are generally disposed inboard from a second longitudinal edge 75B of the substrate 12 during processing. The present invention reduces the slippage of a substrate on the outermost engagement elements of the activation members by providing a non-slip element to at least one of the engagement elements of an activation member.

In contrast with the present invention, conventional activation processes include a plurality of engagement elements which resemble those illustrated in FIGS. 1C and 1D. Consequently, a substrate subjected to the conventional activation process typically slips on the outermost engagement elements of the first and second activation members. This slippage reduces the efficiency of the activation process in that the portions of the substrate nearest the outer ends of the activation members are not strained as much as those portions which are more interiorly located.

Figure 2A:
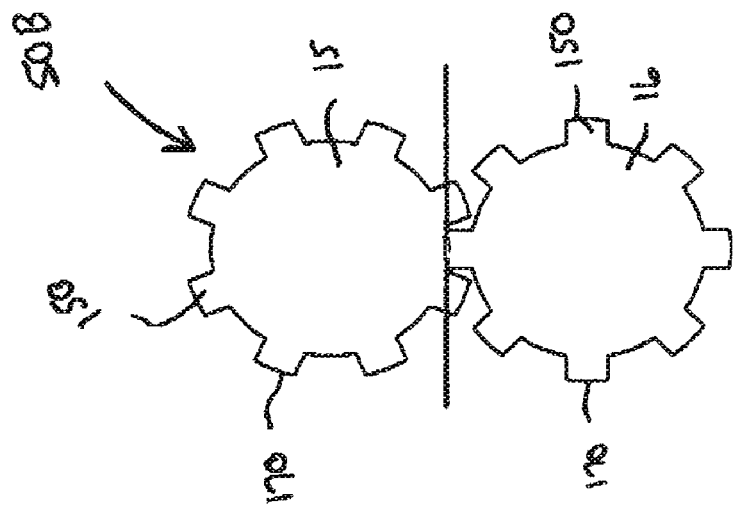
FIGS. 2A and 2B are elevation views showing other embodiments of mechanical activation systems constructed in accordance with the present invention.
Figure 2B:
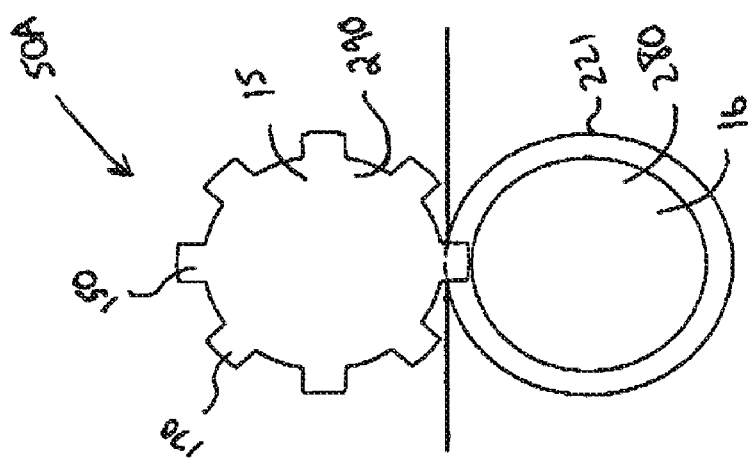

As shown in FIG. 2A, in some embodiments, an activation system 50A may comprise the first activation member 15 and the second activation member 16. As stated previously, a non-slip zone of the present invention may comprise a portion of the first activation member 15 and no portion of the second activation member 16. As such, in some embodiments, the non-slip zone may comprise an engagement element 290 of the first activation member 15 wherein the engagement element 290 has a discontinuous tip 170 and a non-slip element 150. As shown in FIG. 2B, in some embodiments, an activation system 50B may comprise the first activation member 15 and the second activation member 16. Also, as stated previously, a non-slip zone may comprise portion of each of the first activation member 15 and the second activation member 16. Thus, in some embodiments, both the first activation member 15 and the second activation member 16 may each comprise engagement elements having discontinuous tips 170 and non-slip elements 150.

FIGS. 1A-1F and 2A-2B depict examples of mechanical activation systems which are rotary in nature. Specifically, the mechanical activation process involves rotating the first activation member 15 and the second activation member 16. However, embodiments are contemplated where a mechanical activation system includes a linear activation system as opposed to a rotary system. Examples of linear activation systems are discussed hereafter.

Figure 3A:
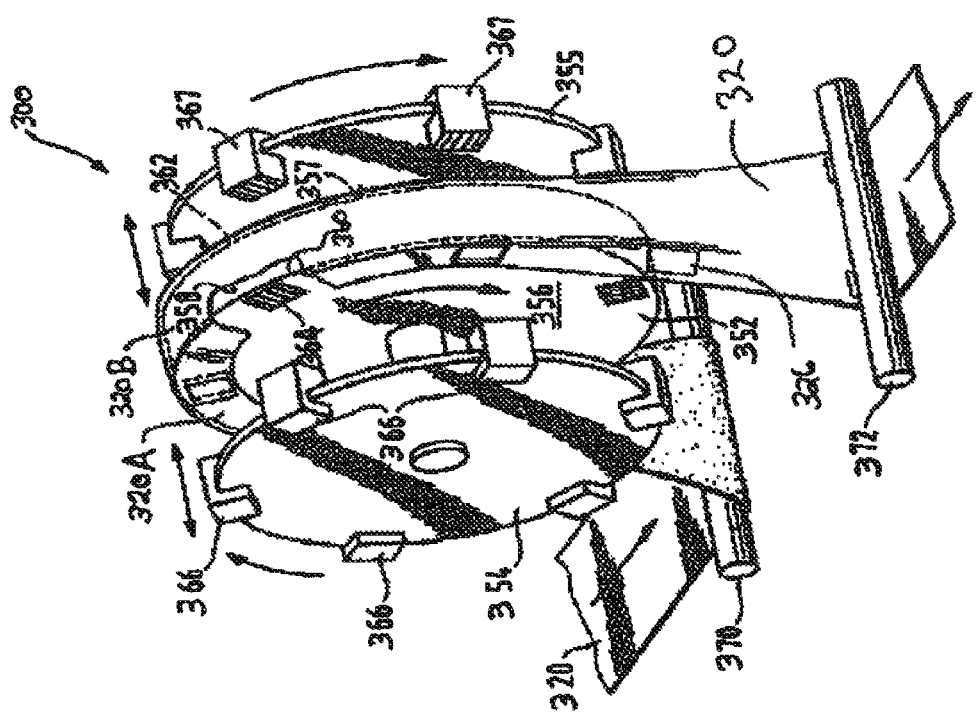
FIG. 3A is an isometric view showing another embodiment of a mechanical activation system constructed in accordance with the present invention.

As shown in FIG. 3A, a mechanical activation system 300, in some embodiments, may comprise a plurality of discs. For example, as shown, in some embodiments, the mechanical activation system 300 may comprise a central disc 352 and a first outer disc 354 and a second outer disc 355. The central disc 352, the first outer disc 354, and the second outer disc 355, can rotate in the direction shown by the arrows associated therewith. Additionally, the first outer disc 354, the second outer disc 355, and the central disc 352 may rotate along the same axis of rotation, in some embodiments.

As shown, the central disc 352 has a first side surface 356 and an opposing second side surface 357. The central disc 352 also has a top surface 358 which spans the distance between the first side surface 356 and the second side surface 357. The first side surface 356 and the second side surface 357 are joined to the top surface 358 at edges 360 and 362, respectively. As shown, the central disc 352 can be configured to carry a web of disposable absorbent articles 320 as discussed in U.S. Pat. No. 6,500,377.

In some embodiments, the first side surface 356 and/or the second side surface 357 are generally orthogonal to the top surface 358. In some embodiments, the first side surface 356 and/or the second side surface 357 may be angled with respect to the top surface 358 at an angle other than 90 degrees. For example, the first side surface 356 and/or the second side surface 357 may be angled relative to top surface 358 at an angle ranging from about 100 degrees to about 90 degrees. In yet another example, the first side surface 356 and/or the second side surface 357 can be angled relative to the top surface 358 at an angle ranging from about 80 degrees to about 90 degrees.

The overall dimensions of the respective discs can be selected as desired. The width of the top surface 358 can be very small, e.g., 1 cm or less, or may be quite large. The diameters of the respective discs can be of any desired dimension. As the diameter of the disc is increased the relative time to activate the web also increases.

As shown, in some embodiments, the central disc 352 may comprise a plurality of activation members 364 disposed on the first side surface 356. Similarly, in some embodiments, a plurality of activation members 365 (shown in FIG. 3B) may be disposed on the second side surface 357 of central disc 352. The number, size, spacing, shape, configuration, etc. of activation members on central disc 352 can be selected by the diaper designer as desired.

Additionally, as shown, the first outer disc 354 may comprise a plurality of activation members 366 which interact with the activation members 364 disposed on the first side surface 356 of the central disc 352. Similarly, the second outer disc 355 may comprise a plurality of activation members 367 which interact with the activation members 365 disposed on the second side surface 357 of the central disc 352. The number, size, spacing, shape, configuration, etc. of activation members on the first outer disc 354 and/or the second outer disc 355 can be selected by the diaper designer to produce the desired effects.

In operation, the activation system 350 can activate select portions of a web of disposable absorbent articles 320. As shown, as portions of the web of disposable absorbent articles 320 are fed past roller 370 and onto the central disc 352, portions of the web are folded over the edges 360 and 362 of the central disc 352. Conventional folding equipment, such as folding boards, may be utilized to fold the web of disposable absorbent articles 320 over the edges 360 and 362 of the central disc 352. Once folded about the central disc 352, the web of disposable absorbent articles 320 has at least two distinct regions, a first region 32013 positioned adjacent top surface 358 and a pair of second regions 320A positioned adjacent the first side surface 356 and the second side surface 357 respectively. The second regions 320A can be held against the first side surface 356 and the second side surface 357 by any suitable means. An example of such suitable means includes vacuum.

As shown, the first outer disc 354 and the second outer disc 355 are spaced apart from the central disc 352 such that the web of disposable absorbent articles 320 can fold about the edges 360 and 362. When the web is folded onto central disc 352 and second regions 320A are held against the first side surface 356 and the second side surface 357, activation members 366 and 367 can be engaged with activation members 364 and 365 on the central disc 352

To cause engagement of the respective activation members, in some embodiments, the activation members of the first outer disc 354 and/or the second outer disc 355 may be moved inwardly towards the activation members of the central disc 352, while the tools of the central disc 352 remain stationary. In some embodiments, the activation members of the first outer disc 354 may move inwardly with respect to the first outer disc 354. In some embodiments, the activation members of the first outer disc 354 may remain stationary with respect to the first outer disc 354 while the first outer disc 354 is translated toward the central disc 354 thereby causing engagement of the respective activation members. The activation members of the second outer disc 355 can be similarly configured.

In some embodiments, the activation members of the central disc 352 may be moved outwardly towards the activation members of the first outer disc 354 and/or the second outer disc 355, while the tools of the first outer disc 354 and/or the second outer disc 355 remain stationary. In some embodiments, the activation members of the first outer disc 354 and/or the second outer disc 355 may be moved inwardly and simultaneously the activation members of the central disc 352 may be moved outwardly to cause engagement of the activation members.

When the desired activation has been achieved, the activation members can be disengaged from one another. To cause disengagement of the respective tools, in some embodiments, the activation members of the first outer disc 354 and/or the second outer disc 355 may be moved outwardly away from the activation members of the central disc 352, while the activation members of the central disc 352 remain stationary. In some embodiments, the activation members of the central disc 352 may be moved inwardly away from the activation members of the first outer disc 354 and/or the second outer disc 355, while the tools of the outer discs remain stationary. In other embodiments, the activation members of the first outer disc 354 and/or the second outer disc 355 may be moved outwardly and simultaneously the activation members of the central disc 352 may be moved inwardly to cause disengagement of the activation members.

The activated web 320 is then removed from the central disc 352 and travels past roller 372. Because the second regions 320A of web of disposable absorbent articles 320 are folded about the central disc 352 onto first side surface 356 and second side surface 357, the time allowed to activate the second regions 320A can be increased compared to that of first zone 320B. As the time allowed for activation is increased, a lower strain is imparted on the web of disposable absorbent articles 320 thus reducing the potential for web damage. Without wishing to be bound by theory, it is believed that because the incremental stretching operation is carried out more slowly, the web is stretched gradually which can reduce the number of defects exhibited by the web as a result of the activation process. The present invention may result in reducing the strain rate activation over prior art systems by as much as 25%, 50%, 100%, or even more.

Figure 3B:
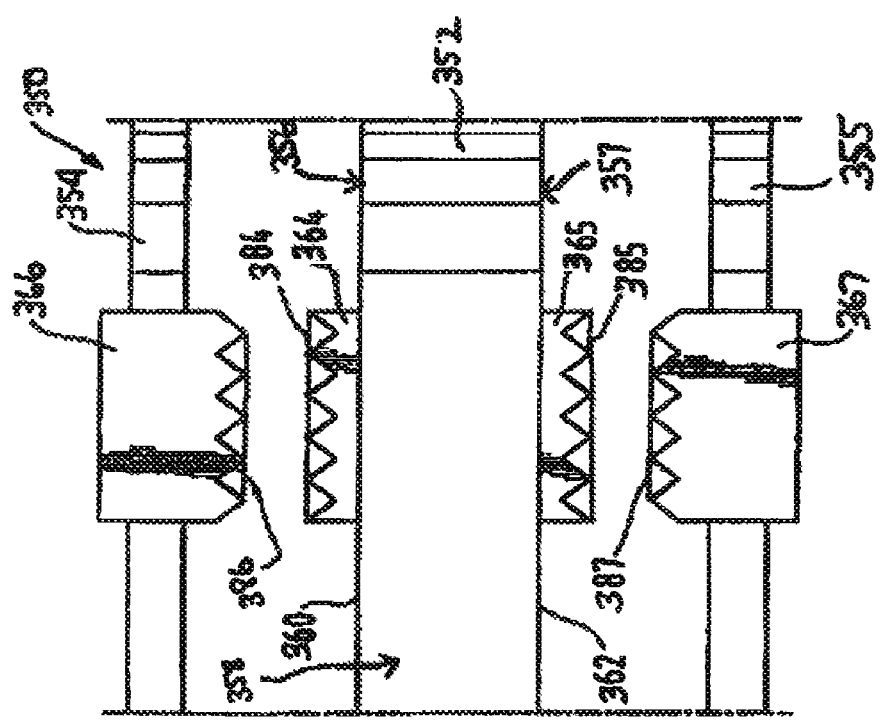
FIG. 3B is a plan view showing a top of the mechanical activation system of FIG. 3A.

As shown in FIG. 3B, the activation members 366 and 364 each comprise a plurality of engagement elements 386 and 384, respectively. Similarly, the activation members 365 and 367 each comprise a plurality of engagement elements 385 and 387, respectively. In general, the timing of the web of disposable absorbent articles 320 (shown in FIG. 3A) is such that elastomeric patches 326 (shown in FIG. 3A) contained within the web of disposable absorbent articles 320 (shown in FIG. 3A) coincide with pairs of activation members 364, 366 and 365, 367, respectively, as the web of disposable absorbent articles 320 (shown in FIG. 3A) travels through activation system 350. In some embodiments, the activation members 364, 366, 365, and/or 367 may be of greater overall dimension than that of elastomeric patches 326 (shown in FIG. 3A) so as to impart a degree of extensibility to those portions of a topsheet and a backsheet which can be adjacent to the elastomeric patches 326 (shown in FIG. 3A).

Other embodiments of activation systems are contemplated. For example, embodiments are contemplated where a mechanical activation system comprises a first disc and a second disc but no central disc. The embodiment is discussed in U.S. Pat. No. 6,500,377.

The exact configuration, orientation, spacing, and depth of the activation members may be varied depending upon such factors as the amount of elasticity desired in the portions of the web comprising the elastomeric patches 326 (shown in FIG. 3A). The degree or depth of engagement of complementary activation members may of course also be adjusted, as desired, to produce more or less extensibility in the web.

Figure 4A:
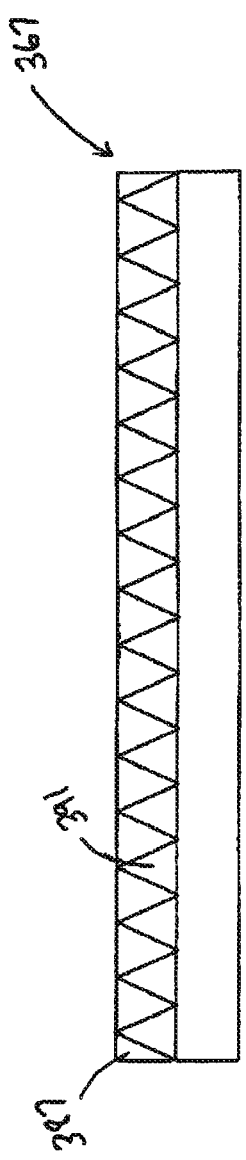
FIG. 4A is an elevation view showing an activation member for use in the mechanical activation system of FIG. 3A.
Figure 4B:
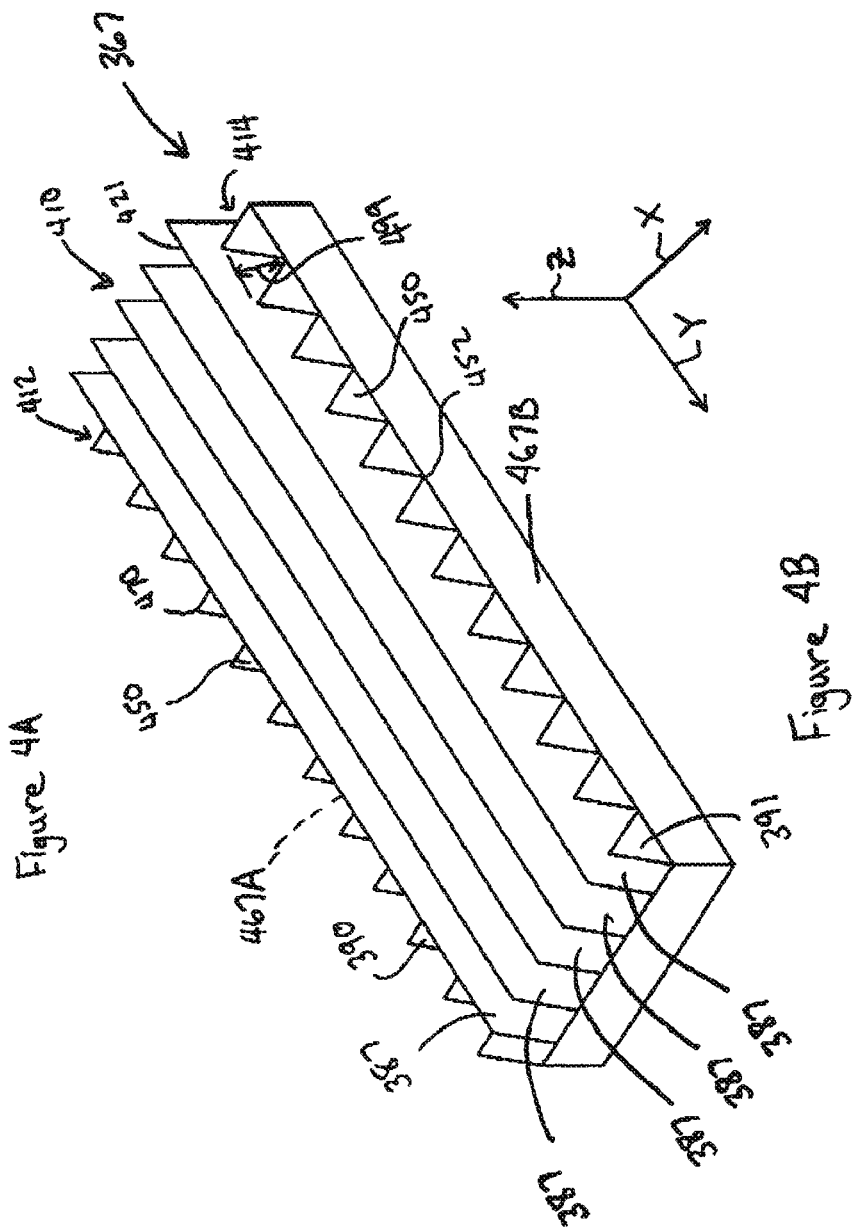
FIG. 4B is an isometric view showing the activation member of FIG. 4A.

As shown in FIGS. 4A and 4B, similar to the activation members of FIGS. 1A and 1B, the activation members of FIGS. 3A and 3B may comprise a non-slip element. The activation member 367 is shown as an example.

The activation member 367 has a first end 467A and a second end 467B. The activation member 367 comprises a plurality of engagement elements 387, 390, and 391. Similar to the activation members described heretofore, the activation member 367 comprises an activation zone 410, a first non-slip zone 412, and a second non-slip zone 414. Embodiments are contemplated where the activation member 367 comprises one non-slip zone and at least one activation zone.

The activation zone 410 may comprise a plurality of engagement elements 387 each having a continuous tip 421. The first non-slip zone 412, in some embodiments, may comprise at least one engagement element 390 having a discontinuous tip 470 and a plurality of non-slip elements 450. In some embodiments, the engagement element 390 can be disposed proximate to the first end 467A of the activation member 367. In some embodiments the first non-slip zone 412 may comprise a plurality of engagement elements each having discontinuous tips.

Similarly, the second non-slip zone 414, in some embodiments, may comprise at least one engagement element 391 having a discontinuous tip 470 and a plurality of non-slip elements 450. In some embodiments, the engagement element 391 can be disposed proximate to the second end 467B of the activation member 367. In some embodiments, the second non-slip zone 414 may comprise a plurality of engagement elements having discontinuous tips.

As shown in FIG. 4A, the addition of the discontinuous tip 470 can produce a plurality of non-slip elements 450 and a plurality of recesses 452. The non-slip elements 450, as shown, in some embodiments, may comprise a triangular shape. However, any suitable shape known in the art can be utilized. For example, the non-slip elements 450 may comprise a square shape, a circular shape, an accurate shape, a rectangular shape, rhomboidal shape, trapezoidal shape, polygonal shape, or any combination thereof.

Additionally, while the embodiment shown in FIG. 4A, shows a plurality of non-slip elements 450, any suitable number of non-slip elements 450 may be utilized. Depending on the specific application, a single non-slip element 450 may provide some reduction in the amount of slippage of the substrate. In other examples, a plurality of non-slip elements 450 may be required. The non-slip elements 450 may be configured as described heretofore with regard to the length 198 (shown in FIGS. 1F and 1G) and the depth 199 (shown in FIGS. 1F and 1G) of the non-slip elements 150 (shown in FIGS. 1F and 1G).

Similar to the engagement elements 190 (shown in FIGS. 1E and 1F) and 191 (show FIG. 1B), a tip 470 which does not extend continuously along the length of a tooth shall be termed discontinuous. Within the context of discontinuous, minor asperities in the tip 470 will not constitute a discontinuous tip. A discontinuous tip comprises a purposefully placed interruption in the tip 470 which produces a non-slip element. Any discontinuities of the present invention should cause recesses which have a depth 499 of between about 0.2 mm to about 5 mm, or any individual number within the range. In some embodiments, the depth 499 can be between about 1 mm to about 3 mm.

Additionally, embodiments are contemplated where, either alternatively or in conjunction with the non-slip elements 450, the first non-slip zone 412 and/or the second non-slip zone 414 comprise engagement elements having an increased coefficient of friction near the tip of the engagement element. Suitable examples of increasing the coefficient of friction of the engagement element are described heretofore.

The depth 499, for the linear activation systems shown with regard to FIGS. 3A-3B and 4A-4B, is the maximum linear distance from a lowest point of a tooth on the activation member to the highest point on the tooth. The depth 499 is generally parallel to a z-axis.

Test Methods

The static coefficient of friction μ between the web surface and activation member can be calculated from the capstan formula as the average coefficient of friction measured at 90 degrees and 180 degrees. This method is applicable to the activation members described herein.

Required Materials:
1. High elongation carded (HEC) nonwoven web (sample web 500) having a basis weight of 27 gsm and dimensions of 50 mm wide and 500 mm long available from BBA Simpsonville.
2. Force gauge 510—Handheld with digital output (e.g., Chatillon DFS series available from Ametek Co., Largo, Fla.). The load cell is chosen such that the forces measured are within 10% to 90% of the limit of the cell.
3. Weight 512 which can be attached to the nonwoven web described in number 1. The weight, when attached to and suspended from the nonwoven induces a strain of 1% in the nonwoven web.

Figure 5A:
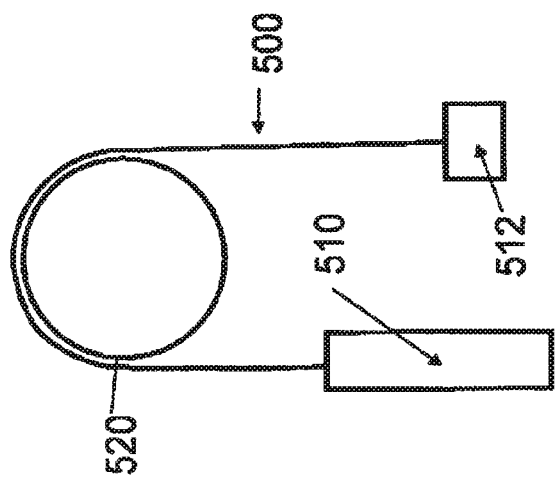
FIGS. 5A and 5B are schematic views showing an exemplary configuration for determining the coefficient of friction of an activation member.
Figure 5B:
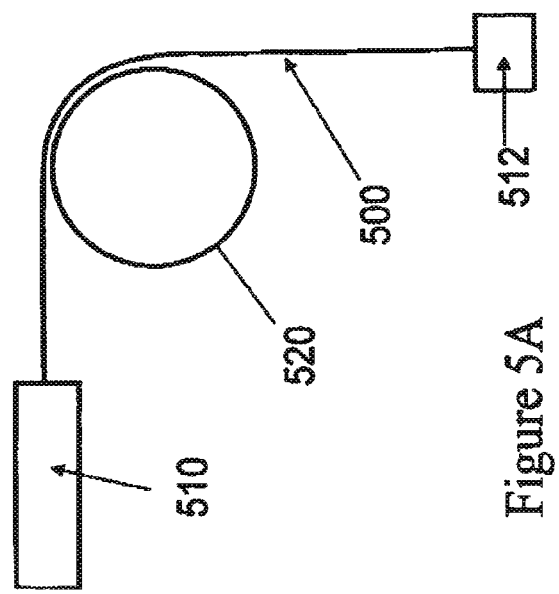

Procedure:
1. As shown in FIG. 5A, the sample web 500 is wrapped around a tooth tip 520 of an activation member.
2. The force gauge 510 is attached to one end of the sample web 500, and the weight 512 is attached to the other end of the sample web 500.
3. Zero the force gauge 510 and then pull at a 90 degree angle with respect to the portion of the sample web 500 which includes the weight 512.
4. At the instant the sample web 500 slips with respect to the activation member 520, the force on the force gauge 510 is measured and recorded.
5. Repeat steps 1-4 four times with four different specimens.
6. Calculate the coefficient of friction $\mu_{90}$ for the 90 degree orientation via the following equation.

$$\mu_{90} = \left(\frac{1}{0.5\pi}\right) * \ln\left(\frac{T_{90}}{W_{90}}\right)$$

where $T_{90}$ is the tension force, in grams of force, measured at 90 degrees on the force gauge.
and $W_{90}$ is the mass, in grams, of the hanged weight 512.
7. Calculate the average $\mu_{90}$ for the four specimens.
8. As shown in FIG. 5B, the sample web 500 is wrapped around an activation member 520.
9. The force gauge 510 is attached to one end of the sample web 500, and the weight 512 is attached to the other end of the sample web 500.
10. Zero the force gauge 510 and then pull at a 180 degree angle with respect to portion of the sample web 500 which includes the weight 512.
11. At the instant the sample web 500 slips with respect to the activation member 520, the force on the force gauge 510 is measured and recorded,
12. Repeat steps 8-11 four times with four different specimens.
13. Calculate the coefficient of friction $\mu_{180}$ for the 180 degree orientation via the following equation.

$$\mu_{180} = \left(\frac{1}{\pi}\right) * \ln\left(\frac{T_{180}}{W_{180}}\right)$$

where $T_{180}$ is the tension force, in grams of force, measured at 180 degrees on the force gauge.
and $W_{180}$ is the mass, in grams, of the hanged weight 512.
14. Calculate the average $\mu_{90}$ for the four specimens.
15. Calculate the overall static coefficient of friction μ by averaging the $\mu_{90}$ and $\mu_{180}$ values.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of mechanically activating a substrate comprising the steps of:
obtaining a substrate;
providing the substrate to a mechanical activation system;
intermeshing the substrate between a first plurality of engagement elements of a first activation member and a second plurality of engagement elements of a second activation member; and
reducing slippage of the substrate with respect to the first activation member and the second activation member in the cross-direction by providing a portion of the first plurality of engagement elements or a portion of the second plurality of engagement elements with discontinuous tips,
the discontinuous tips comprising a coating, the coating having a coefficient of friction from about 0.8 to about 1.0.

2. The method of claim 1 wherein the substrate is a nonwoven material.

3. The method of claim 1 wherein the substrate is a laminated structure comprising a nonwoven material joined to an elastic.

4. The method of claim 1 wherein a portion of the first plurality of engagement elements and a portion of the second plurality of engagement elements comprise discontinuous tips.

5. The method of claim 1, wherein the portion of the plurality of engagement elements comprising discontinuous tips defines a non-slip zone, and the non-slip zone is disposed proximate to a first end or a second end of the plurality of engagement elements.

6. The method of claim 5, wherein a non-slip zone is disposed proximate to each of a first end and a second end of the plurality of engagement elements.

7. The method of claim 5, wherein the non-slip zone comprises engagement elements from the first plurality of engagement elements.

8. The method of claim 5, wherein the non-slip zone comprises engagement elements from the second plurality of engagement elements.

9. The method of claim 7, wherein the non-slip zone comprises engagement elements from the second plurality of engagement elements.

10. The method of claim 5, wherein the non-slip zone comprises two or more engagement elements.

11. The method of claim 1, wherein the discontinuous tips comprise non-slip elements having a shape selected from the group consisting of triangular, circular, arcuate, rectangular, rhomboidal, trapezoidal, polygonal, and combinations thereof.

12. The method of claim 1, wherein the first and second plurality of engagement elements are disposed on discs.

13. The method of claim 1, wherein the first and second plurality of engagement elements are disposed on plates.

14. The method of claim 1, wherein the discontinuous tips comprise discontinuities having a depth between 0.2 mm and 5 mm.

* * * * *